(12) United States Patent
Pouillot et al.

(10) Patent No.: US 9,029,153 B2
(45) Date of Patent: May 12, 2015

(54) MODIFICATION OF THE GENOME OF A LYTIC BACTERIOPHAGE BY IMMOBILIZING SAID BACTERIOPHAGE IN THE HOST BACTERIUM THEREOF

(75) Inventors: Flavie Pouillot, Paris (FR); Francois Iris, Chaville (FR)

(73) Assignee: Pherecydes Pharma (FR)

( * ) Notice: Subject to any disclaimer, the term of this patent is extended or adjusted under 35 U.S.C. 154(b) by 374 days.

(21) Appl. No.: 13/266,836

(22) PCT Filed: Apr. 27, 2010

(86) PCT No.: PCT/FR2010/050796
§ 371 (c)(1),
(2), (4) Date: Oct. 28, 2011

(87) PCT Pub. No.: WO2010/125296
PCT Pub. Date: Nov. 4, 2010

(65) Prior Publication Data
US 2012/0040465 A1    Feb. 16, 2012

(30) Foreign Application Priority Data

Apr. 30, 2009 (FR) ..................................... 09 52933

(51) Int. Cl.
| | | |
|---|---|---|
| *C07K 14/005* | (2006.01) | |
| *C07K 14/245* | (2006.01) | |
| *C12N 15/02* | (2006.01) | |
| *C12N 15/70* | (2006.01) | |
| *C12N 11/16* | (2006.01) | |
| *C12N 15/10* | (2006.01) | |

(52) U.S. Cl.
CPC ............ *C12N 15/102* (2013.01); *C07K 14/005* (2013.01); *C12N 11/16* (2013.01); *C12N 2795/10122* (2013.01)

(58) Field of Classification Search
None
See application file for complete search history.

(56) References Cited

FOREIGN PATENT DOCUMENTS

| FR | 102007003148 | * | 7/2008 |
| WO | 2008/093009 A2 | | 8/2008 |

OTHER PUBLICATIONS

International Search Report, PCT/FR2010/050796, dated Aug. 16, 2010.
Xu Yi et al: "Mutations in the Rho transcription termination factor that affect RNA tracking" Journal of Biological Chemistry, vol. 277, No. 33, Aug. 16, 2002, pp. 30023-30030, XP002562011.
Miwa Yoshihiro et al: "Structural and functional dissections of transcription termination factor Rho by random mutagenesis" Journal of Molecular Biology, London, GB, vol. 254, No. 5, Jan. 1, 1995, pp. 815-837, XP002241067.
Martinez A et al: "Mutational analysis and secondary structure model of the RNPI-like sequence motif of transcription termination factor rho" Journal of Molecular Biology, London, GB, vol. 257, No. 5, Jan. 1, 1996, pp. 895-908, XP002353473.
Yoichi M et al: "Alteration of tail fiber protein gp38 enables T2 phage to infect *Escherichia coli* 0157:H7" Journal of Biotechnology, Elsevier Science Publishers, Amsterdam, NL, vol. 115, No. 1, Jan. 12, 2005, pp. 101-107, XP004966993.
Castilla-Llorente Virginia et al: "kinC/D-mediated heterogeneous expression of spoOA during logarithmical growth in *Bacillus subtilis* is responsible for partial suppression of phi 29 development" Molecular Microbiology, vol. 68, No. 6, Jun. 2008, pp. 1406-1417, XP002562013.
Pouillot Flavie et al: "Genetically engineered virulent phage banks in the detection and control of emergent pathogenic bacteria." Biosecurity and Bioterrorism : Biodefense Strategy, Practice, and Science Jun. 2010 LNKD—PUBMED:20569057, vol. 8, No. 2, Jun. 2010, pp. 155-169, XP002594997.

* cited by examiner

*Primary Examiner* — Nita M Minnifield
(74) *Attorney, Agent, or Firm* — Lerner, David, Littenberg, Krumholz & Mentlik, LLP (57) ABSTRACT

The present invention relates to a method for the reversible immobilization of lytic bacteriophages within their modified bacterial hosts.
It relates more particularly to a method for modifying the genome of a lytic bacteriophage by immobilizing said bacteriophage in the host bacterium thereof.

14 Claims, 3 Drawing Sheets

Construction of a host bacterium with the mutated *rho* gene
in an inducible vector

↓

Induction of the mutated *rho* gene

↓

Infection with the lytic bacteriophage

↓

Immobilization of the lytic bacteriophage DNA in the host
bacterium due to overexpression of mutated rho

↓

Modification of the bacteriophage genome

↓

Cessation of mutated *rho* gene induction: release
of the bacteriophage DNA

↓

Recovery of new phage particles

SEQUENCE LISTING

```
<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: RhoF primer for amplification of rho gene
<220> FEATURE:
<221> NAME/KEY: primer_bind
<222> LOCATION: (1)..(31)
<223> OTHER INFORMATION: RhoF primer for amplification of rho gene

<400> SEQUENCE: 1
caccatgaat cttaccgaat taaagaatac g                              31

<210> SEQ ID NO 2
```

```
<211> LENGTH: 23
<212> TYPE: DNA
<213> ORGANISM: Artificial Sequence
<220> FEATURE:
<223> OTHER INFORMATION: RhoR primer for amplification of rho gene
<220> FEATURE:
<221> NAME/KEY: primer_bind
<222> LOCATION: (1)..(23)
<223> OTHER INFORMATION: RhoR primer for amplification of rho gene

<400> SEQUENCE: 2
ttatgagcgt tcatcattt cga                                        23

<210> SEQ ID NO 3
<211> LENGTH: 19
<212> TYPE: DNA
<213> ORGANISM: Artificial Sequence
<220> FEATURE:
<223> OTHER INFORMATION: MlambdaRf primer for amplification prophage
      lambda cl857
<220> FEATURE:
<221> NAME/KEY: primer_bind
<222> LOCATION: (1)..(19)
<223> OTHER INFORMATION: MlambdaRf primer for amplification prophage
      lambda cl857

<400> SEQUENCE: 3
gtatgcatgc tgggtgtgg                                            19

<210> SEQ ID NO 4
<211> LENGTH: 25
<212> TYPE: DNA
<213> ORGANISM: Artificial Sequence
<220> FEATURE:
<223> OTHER INFORMATION: MlambdaRr primer for amplification prophage
      lambda cl857
<220> FEATURE:
<221> NAME/KEY: primer_bind
<222> LOCATION: (1)..(25)
<223> OTHER INFORMATION: MlambdaRr primer for amplification prophage
      lambda cl857

<400> SEQUENCE: 4
cgcactctcg attcgtagag cctcg                                     25

<210> SEQ ID NO 5
<211> LENGTH: 24
<212> TYPE: DNA
<213> ORGANISM: Artificial Sequence
<220> FEATURE:
<223> OTHER INFORMATION: MobaF primer for amplification of T4 mobA gene
<220> FEATURE:
<221> NAME/KEY: primer_bind
<222> LOCATION: (1)..(24)
<223> OTHER INFORMATION: MobAF primer for amplification of T4 mobA gene

<400> SEQUENCE: 5
gtagaaaata gtgctaaaaa gtgt                                      24

<210> SEQ ID NO 6
<211> LENGTH: 22
<212> TYPE: DNA
<213> ORGANISM: Artificial Sequence
<220> FEATURE:
<223> OTHER INFORMATION: MobaR primer for amplification of T4 mobA gene
<220> FEATURE:
<221> NAME/KEY: primer_bind
```

```
<222> LOCATION: (1)..(22)
<223> OTHER INFORMATION: MobAR primer for amplification of T4 mobA gene

<400> SEQUENCE: 6
ttaatagtgc ggggtaaaac cc                                            22
```

MODIFICATION OF THE GENOME OF A LYTIC BACTERIOPHAGE BY IMMOBILIZING SAID BACTERIOPHAGE IN THE HOST BACTERIUM THEREOF

CROSS-REFERENCE TO RELATED APPLICATIONS

This application is a national phase entry under 35 U.S.C. §371 of International Application No. PCT/FR2010/050796 filed Apr. 27, 2010, published in French, which claims priority from French Patent Application No. 0952933, filed Apr. 30, 2009, all of which are incorporated herein by reference.

SEQUENCE LISTING

The instant application contains a Sequence Listing which has been submitted in ASCII format via EFS-Web and is hereby incorporated by reference in its entirety. Said ASCII copy, originally filed in a priority document on Jan. 15, 2010, is named B090081USA Sequence listing.txt and is 2,308 bytes in size.

BRIEF SUMMARY OF THE INVENTION

Bacteriophages are viruses having a size from about 24 to 200 nm, capable of infecting bacteria specifically.

Bacteriophages, in their free form, are constituted by an external protein coat, called the capsid, containing the genetic material, which constitutes their genome. The genome of the vast majority of bacteriophages is constituted by a linear double-stranded DNA molecule with a size between about 5 and 650 kb. The capsid generally has a tail extension serving for injecting said genetic material into the host bacterium.

A great variety of bacteriophages exist in nature.

However, bacteriophages are generally very specific and can only infect a very small number of bacterial species. This narrow specificity is linked, in particular, with their mechanism of penetration into the bacterial cell: phages are capable of specifically recognizing the glycoprotein structures present on the surface of the wall of their host bacterium, which they utilize as "receptors". These structures allow them to attach to the wall and inject their genetic material into the cytoplasm of their host bacterium. This recognition takes place by means of so-called "targeting" proteins, which are present on the surface of the capsid or at the end of the filaments of the bacteriophage, also called "tail fibres".

The bacteriophages are classified on the basis of their replication cycles. Thus, there are three main categories of bacteriophages:

Bacteriophages in the first category are called "lytic" or "virulent", i.e. immediately after they infect a bacterium, the expression and replication of their genome lead to the production of new phage particles, and, after a short time, cause lysis of the host bacterium and the release of multiple progeny.

The bacteriophage T4, for example, is a bacteriophage that infects the bacterium *Escherichia coli*. Its lytic cycle takes about 30 minutes at 37° C. This cycle begins immediately after recognition of the host bacterium by the bacteriophage, with a phase of absorption and penetration. It is reflected in the immediate switching from the expression of the genes of the host bacterium to those of the bacteriophage, permitting synthesis of the enzymes required for replication of the bacteriophage. Then, about 10 minutes after infection, DNA replication and synthesis of viral proteins take place, and assembly of daughter bacteriophages (starting after 12 minutes). The replication cycle leads to the bursting of the bacterium (after 30 minutes) and the release of about fifty bacteriophages per lysed bacterium into the environment.

A second category of bacteriophages are called "lysogenic" or "temperate". These bacteriophages can remain in a quiescent state, integrating their genetic material with that of the bacterium. This is then called provirus or prophage, i.e. a virus whose genetic material is integrated with the chromosome of the host bacterium. The bacteriophage genome is copied at each cell division with all of the DNA of the bacterium, which is then termed lysogenic. During this phase of latency, the expression of the genes encoded by the phage genome is generally repressed by a repressor protein. Under certain conditions, especially in the case of deficiency or stress, the prophage comes out of its quiescent state and activates its replication cycle. It is excised from the genome of the host and enters a lytic cycle, as described above.

A third category of bacteriophages do not cause lysis of the infected cell, but rather bud on the surface of the bacterial membrane, without breaking it. This is the case with the filamentous bacteriophages of the type M13 or f1 of *Escherichia coli*, which are used in the well-known techniques of "phage display". The infected bacterium survives the infection and produces bacteriophages continuously.

The present invention relates to the first category of bacteriophages called "lytic" mentioned above.

The lytic bacteriophages have the particular feature of killing the bacteria that they infect, which makes it possible to use them as antibacterial agents.

The idea of using preparations of lytic bacteriophages for combating bacterial infections is by no means new, dating back to the time before antibiotics were discovered.

The efficacy of bacteriophages for combating bacterial infections has been demonstrated. However, their use has remained very marginal relative to that of antibiotics. The spectrum of activity of bacteriophages is in fact much narrower than that of the antibiotics, which considerably limits their interest, in particular, in the area of preventive treatments.

Today, faced with the appearance of bacterial strains that are multi-resistant to antibiotics and with the difficulties encountered by the scientific community in developing new antibiotics, there has been a revival of interest in bacteriophages, in particular for combating nosocomial infections [Thiel, K., *Nature Biotechnology*, 2004, 22:31-36], i.e. against targeted, multi-resistant or emergent bacteria.

In a previous application WO 2008/093009, the present inventors described a method for obtaining recombinant bacteriophages whose targeting proteins were modified at random. This modification is carried out by inserting, into the genes coding for the targeting proteins, oligonucleotide sequences produced randomly, so that the bacteriophages obtained acquire the capacity to recognize and infect new bacteria, preferably different from their usual host.

Obtaining such bacteriophages, having a spectrum that is broader or different from that of their host bacterium, represented a challenge, because when the targeting proteins of a bacteriophage are modified, the latter can lose its ability to recognize its host. As a result it cannot be reproduced, nor maintained in its host.

To overcome this difficulty, the inventors proposed, in their previous invention, creating a bank of host bacteria comprising a plurality of homologous recombination vectors, within which randomly produced nucleotide sequences were cloned. These bacteria were infected en masse by bacteriophages, in such a way that the largest possible number of random sequences contained in these vectors will be inserted by homologous recombination in the genes coding for the targeting proteins. The recombinant bacteriophages thus modified were recovered after a single cycle of lytic replication to form a bank of diversified bacteriophages. Said bank of bacteriophages is then stored, with a view to being used against target bacteria that we wish to eradicate or control.

However, this invention, as well as most of the methods of modifying lytic bacteriophages, have the limitation that replication of the bacteriophages takes place in a short space of time, which corresponds to the duration of the lytic cycle.

Now, to be able to preserve the diversity of the modified bacteriophages, more particularly those whose targeting proteins have been modified, it is important to recover the first-generation bacteriophages at the end of the first cycle of infection. If the bacteriophages infect their host again, this causes their diversity to decrease, because only the bacteriophages recognizing their host are reproduced.

This temporal limitation, linked to the duration of the lytic cycle, reduces the frequency of the genetic recombination events, and therefore limits the diversity of the modified bacteriophages that can result therefrom.

Another limitation, independent of the first, resides in the fact that the bank of modified bacteriophages obtained cannot be reproduced. It therefore necessary, in order to produce a new stock of modified bacteriophages, once again to infect a stock of host bacteria having a plurality of vectors permitting insertion of random sequences.

The present invention aims to overcome these limitations, and more particularly, to overcome the constraints associated with the lytic cycle imposed by bacteriophages of this type.

The inventors found, surprisingly, that by overexpressing a modified form of the Rho protein in a bacterium infected by a bacteriophage, it was possible to inhibit the lytic cycle of the phage in this bacterium and prevent, at least temporarily, the production of progeny of the bacteriophage and lysis of the bacteria.

Based on this inhibition, the inventors developed a method for immobilizing a lytic bacteriophage once it enters a host bacterium.

By "immobilization", it is meant that the bacteriophage, or rather its genome, is retained within the host bacterium in a controlled manner.

To the best of their knowledge, it is the first time that a lytic phage has been immobilized in this way, inducibly, within its host bacterium.

It must be borne in mind that replication of the genome of bacteriophages is a very complex process, which is thought to be independent of the duplication of the bacterial chromosomes. This replication involves steps of DNA transcription, translation and duplication.

Inhibition of the lytic cycle according to the invention does not appear to affect significantly the process of duplication of DNA, in particular, of the bacterial genome. Thus, the inventors established that it was possible to modify, very effectively, the bacteriophage genome in the bacterium during its period of immobilization.

Moreover, during the so-called period of immobilization, the integrity of the bacterium is preserved, so that it can be transformed, in particular by electroporation. Accordingly, the bacteriophage genome can be modified within the bacterium, in particular by homologous recombination, involving exogenous genetic material such as PCR fragments or vectors.

The modified forms of the Rho protein, which were used by the inventors to achieve immobilization of the bacteriophages according to the invention, result more particularly from the expression of mutated forms of rho genes.

Rho genes are present in the genome of numerous bacterial species. It is therefore sufficient, according to the invention, to obtain a mutated copy of the wild-type gene present in a given bacterial species, to be able to obtain immobilization of the bacteriophages specific to this given species and, if required, proceed to the modification of its genome.

The method of the invention, as well as the host bacteria developed by the inventors, therefore constitute novel tools of molecular biology making it possible to immobilize and modify the genome of lytic bacteriophages in a very large number of bacterial hosts.

The invention has many advantages, detailed hereunder, which in particular reside in the fact that:
  the bacteriophage is immobilized effectively, stably and in a completely controlled manner, by simple means that can be applied in any potential bacterial host;
  the immobilization of the bacteriophage is reversible and affects neither its lytic character, nor its capacity for replication once the immobilization is removed;
  the mechanism of immobilization withstands electroporation and permits multiple successive recombination steps on the bacteriophage without adversely affecting the host and without having recourse to successive lytic cycles, which, owing to successive infections, lead, by selection with respect to the host, to a loss of diversity of the bacteriophages;
  the bacteriophage immobilized in the host can act as a "modulable transduction vector", i.e. it can participate in the transformation of its host or can be inserted in the genome of its host, in the manner of a lysogenic bacteriophage;
  the infected host bacterium has the particular feature of becoming resistant to any subsequent infection by another bacteriophage, which limits horizontal transfers of DNA and increases the reliability of the method of modification of the genome.

DETAILED DESCRIPTION OF THE INVENTION

In its general principle, the invention relates to a method making it possible to immobilize and modify the genome of a lytic bacteriophage in a host bacterium. This method is characterized, in particular, in that:

(i) a host bacterium is infected with a bacteriophage;

(ii) the lytic cycle of the bacteriophage in its host is inhibited temporarily;

(iii) the bacteriophage genome is modified during step ii) during which the bacteriophage is immobilized in the host bacterium;

(iv) the inhibition of the lytic cycle induced in step ii), which can be described as temporary, is removed so as to release the progeny of the bacteriophage of step (i) the genome of which was modified. The progeny, constituting the descendants of the bacteriophage, comprises daughter bacteriophages, a proportion of which comprises a genome that has been modified relative to that of the parent bacteriophage, which was used for infecting the host bacterium.

By modification of the genome of a bacteriophage, it is meant any altering of the initial genetic material of a bacteriophage, regardless of the technique used for achieving this. It may be point mutations, insertions or deletions. The present invention more particularly facilitates modifications of the genome involving the techniques of homologous recombination. The techniques of homologous recombination used for carrying out the present invention are known to a person skilled in the art [Poteete, A. R. et al., (2001) FEMS Microbiol. Lett. 201 (1):9-14; Kuzminov, A. et al. (2001) PNAS, 98 (15):8298-305].

Preferably, the bacteriophage, the genome of which is modified according to the invention, is a bacteriophage of the Myoviridae family, preferably of T type, such as the bacteriophages T4, T5, T6 and T7. These bacteriophages are well known to a person skilled in the art, especially the bacteriophage T4, the complete genome of which has been sequenced [Miller, E. S. et al., Bacteriophage T4 genome, Microbiol Mol. Biol. Rev., 2003, 67 (1):86-156]. The complete sequence of the bacteriophage genome is available in Genbank (AF 158101).

A host bacterium according to the invention is a bacterium commonly used for replicating the bacteriophages, the genome of which one wishes to modify. Preferably, the host bacterium is a strain that can be transformed by means of a DNA construct according to the invention, making it possible to modify the bacteriophage by homologous recombination.

A host bacterium particularly suitable for the T type bacteriophages for implementing the method of the present invention is a Gram-negative bacterium, more particularly Escherichia coli. The DK8 strain (ATCC 47038) is particularly suitable for modifying the bacteriophage T4.

In the context of the modification of the genome of bacteriophages of type T, it may be advantageous to use a strain of E. coli transformed by means of a vector of the Mini-lambda type (A), derived from the lambda prophage and comprising the genes exo, bet and gam. A vector of this kind makes it possible to control, for example, homologous recombination, as a function of the temperature at which the host bacterium is cultured, and thus better control the recombination events taking place in the host bacterium.

By "inhibition of the lytic cycle" is meant increasing the duration of the lytic cycle relative to the normal duration of said lytic cycle. The normal duration of the lytic cycle can be established experimentally (uninhibited control) or can be obtained from data in the literature for experiments conducted under comparable experimental conditions. Preferably, the inhibition is such as to limit the number of bacteria infected, in which the phenomenon of lysis and of release of the bacteriophages is observed, to less than 20%, preferably less than 10%.

Inhibition of the lytic cycle is preferably obtained transiently, in such a way that the immobilization of the bacteriophage in the bacterium is temporary, i.e. limited in time. Preferably, the inhibition is reversible. The invention in fact envisages reactivation of the cycle after modification of the genome, in order to be able to recover the bacteriophages released by the bacterium. The modified bacteriophages then constitute the progeny of the bacteriophage that initially infected the bacterium and the genome of which was modified during the immobilization step. This reactivation is preferably achieved by removing the inhibition of the lytic cycle.

However, according to one aspect of the invention, the immobilization of the bacteriophage can be provided over a very long time, in particular for preserving the bacteriophage genome, modified or not, in its immobilized form, in the host bacterium. It can, for example, be envisaged to freeze the host bacteria after step ii) or step iii), and thus postpone step iv) mentioned above.

Preferably, the lytic cycle of the bacteriophage is inhibited in step ii) in the host bacterium, by the expression, in the cytoplasm of the bacterium, of a protein having the effect of interfering with the initial phase of the replication cycle, in particular, of limiting or preventing production of the proteins necessary for transcription of the genes of the bacteriophage. This interfering protein can be expressed in the cytoplasm of the bacterium by means of an expression vector, preferably from a genetic sequence placed under the control of an inducible promoter. Genetic constructs of this kind are well known to a person skilled in the art [Sambrook J., Russel D. W. (2001) Molecular Cloning, a Laboratory Manual, CHSL Press]. Examples of inducible promoters are those of the GAL type, inducible by the addition of IPTG, or of the HSP type, inducible by heat shock.

Preferably, the expression of the protein that permits the inhibition of the replication cycle (lytic cycle) of the bacteriophage is induced before infection, i.e. before the host bacterium is brought into contact with the bacteriophage.

According to a preferred aspect of the invention, the lytic cycle is inhibited by means of a mutated form of the Rho protein, called Rho*, or of a homologous protein of the latter. The Rho protein is a protein that is present in most bacteria, especially the Gram-negative bacteria. By homologous is meant a protein having the same characteristics as Rho, preferably the same function, in particular having a percentage identity of amino acids greater than 40% of the latter, preferably greater than 60%, more preferably greater than 80% and even more preferably greater than 95%.

The Rho protein and its various forms are described extensively in the literature [Pinkham, J. L et al. (1983) The nucleotide sequence of the rho gene of E. coli K-12 Nucleic Acids Res. 11 (11):3531-3545] [EMBL J01673]. It has been established that this protein, in its functional form, is involved in termination of transcription [Hitchens, T. K. (2006) Sequence specific interactions in the RNA-binding Domain of E. coli Transcription Factor Rho*, J. Biol. Chem. 281 (44):33697-

703]. Many mutant forms of this protein (Rho*), regarded as non-functional, are described in the literature. Mutation of the rho gene in *E. coli* has the effect of greatly decreasing growth of the bacteria, to such a degree that it is regarded as an essential gene [Chalissery, J. (2007) Transcription Termination in Defective mutants of Rho: Role of different Functions of Rho in releasing RNA from the Elongation complex, *J. Mol. Biol.* 371 (4):855-872]. The absence of functional Rho protein in *E. coli* disturbs the replication cycle of the bacteriophages [Linder, H. C. (1985) *E. coli* Rho Factor is involved in Lysis of Bacteriophage T4-infected cells, *Genetics* 111: 197-218]. However, many questions remain concerning the manner in which Rho is involved in the replication cycle of the bacteriophages [Banerjee S. (2006) Rho-dependent Transcription Termination: More questions than answers. *J. Microbiol.* 44 (1):11-22].

Preferably, it is a mutated Rho* form, considered to be non-functional, that makes it possible to obtain immobilization of bacteriophages when it is expressed in the cytoplasm of the infected host bacterium. By "non-functional", it is meant a mutated form of the wild-type protein, which is unable to provide the function that it usually performs in the cell. A great many non-functional mutants of Rho are described in the literature [*J. Mol. Biol.* (2007) 371 (4):855-872], such as, for example, those having substitutions in the wild-type sequence of Rho at the following amino acids: G51V, G53V, Y80C, Y274D, P279S, P279L, G324D, N340S and 1382N.

Therefore, a preferred aspect of the invention resides in overexpression of Rho* proteins in a host bacterium infected by a bacteriophage, in order to inhibit the lytic cycle of said bacteriophage.

Preferably, this expression is obtained on the basis of a copy of the wild-type gene present naturally in the bacterium, said copy having been mutated and generally cloned into an expression vector. The mutated copy of the gene is preferably overexpressed in parallel with the wild-type rho gene, which is generally present on the bacterial chromosome.

Surprisingly, the inventors have observed that the expression of a Rho* protein in the bacterium resulted in the inhibition of the replication cycle of the bacteriophage, even if the wild-type Rho protein is expressed in the bacterium in a functional form.

In this respect, the invention relates more particularly to a method as defined above, comprising one or more of the following steps:

i) culturing a host bacterium possessing a rho gene, as well as a mutated copy of said gene (rho*), the expression of which is optional;

ii) inducing the expression of the mutated rho* gene in the host bacterium;

iii) infecting this host bacterium in which the mutated rho* gene is expressed by means of a lytic bacteriophage which is specific to it, which has the effect of immobilizing the bacteriophage in its host bacterium;

iv) modifying the bacteriophage genome within the host bacterium during step iii);

v) ceasing to induce the expression of rho* by allowing the wild-type rho gene to be expressed in the bacterium, which has the effect of removing the immobilization of the bacteriophage and releasing its progeny, the genome of which has been modified.

It is advantageous according to the invention to conserve a copy of the functional wild-type rho gene in the host bacterium, in parallel with the mutated rho* copy. It appears, in fact, that the expression of the Rho [+] protein enables the bacterium to continue dividing throughout immobilization of the bacteriophage. It is thus possible to allow the host bacterium to divide while the bacteriophage is immobilized, in particular between steps iii) and iv) of the method. The inventors thus saw that while it was immobilized, the bacteriophage genome was replicated at the same time as that of its host. Accordingly, it is possible to increase the number of cells in which the bacteriophages are immobilized by division of the host bacteria, and thus easily increase the number of bacteria in which the bacteriophages are immobilized during the method.

Without being bound by theory, the inventors hypothesized that the Rho* protein had the capacity to compete with the wild-type Rho protein.

However, according to current knowledge, it is difficult to evaluate whether the Rho protein is involved specifically in the lytic cycle of the bacteriophage or, more generally, whether it acts on the set of mechanisms of duplication (or of transcription) of the genetic elements present in the bacterium.

An additional advantage of the invention is that during the immobilization phase of the bacteriophage, the host bacterium is still able to receive nucleic acid sequences of exogenous origin. In particular, it is possible to make, for example, PCR fragments, cDNAs, RNAs or vectors penetrate into their cytoplasm, and thus transform these bacteria genetically, in particular, by electroporation, i.e. by applying an electric field. This method is well known to a person skilled in the art [Dunny, G. M. et al. (1991) Improved electroporation and cloning system for gram-positive bacteria. Appl. Environ. Microbiol. 57:1194-1201] [Reysset, G. (1993) Transformation and electrotransformation in clostridia, p. 111-119. In M. Sebald (ed.), Genetics and molecular biology of anaerobes. Springer-Verlag, New York N.Y.] [Sambrook, J. and D. W. Russell (2001). Molecular cloning: a laboratory manual, 3rd ed. Cold Spring Harbor Laboratory Press, Plainview, N.Y.]. One aspect of the invention is therefore that it is possible to modify the bacteriophage genome during its immobilization, by transformation of the host bacterium. Preferably, the transformation is carried out by means of one or more vectors, in particular a vector for homologous recombination.

The transformation of the host bacterium can take place before or during step iii) corresponding to the immobilization phase. In particular, the host bacterium can be transformed by means of a DNA or RNA of exogenous nature before being infected by the bacteriophage.

According to one aspect of the invention, some or all of the bacteriophage genome can be inserted into a vector by homologous recombination present in the bacterium, during the immobilization phase, as indicated in the examples.

Another aspect of the invention relates to preparation of a host bacterium permitting implementation of the method described above. Such a host bacterium, more particularly, comprises a bacterium containing a mutated copy of the rho gene (rho*), preferably present on an expression vector, permitting the expression of Rho* proteins. In general, the host bacterium according to the invention further comprises a copy of the rho gene on its chromosome permitting the expression of wild-type Rho proteins.

When said host bacterium is infected by a bacteriophage, the former further comprises, in its cytoplasm, the genome of said bacteriophage.

A host bacterium that is preferred according to the invention is more particularly a bacterium (Rho*-λ) as described in the examples of the present application.

The present application also relates to a kit for implementing the method according to the invention, comprising one or more elements according to the invention selected from the following:

a host bacterium as defined above, an expression vector comprising a copy of the mutated rho gene (rho*), preferably placed under the control of an inducible promoter, a homologous recombination vector enabling the bacteriophage genome to be modified, reagents or culture media for culturing the host bacterium and inducing immobilization of the bacteriophage in said host bacterium.

The present invention is particularly suitable for the production of bacteriophages whose targeting proteins have been modified.

In particular, the invention envisages that the genome of a bacteriophage should be modified in step iii) of the method described previously, at the level of a gene expressing a targeting protein, preferably a gene coding for the GP12, GP36, GP37 and GP38 proteins or proteins homologous with the latter.

The targeting proteins of the bacteriophage are defined as proteins that participate in the bacteriophages' recognition of and adhesion to the host bacterium. These proteins are preferably selected from those constituting the tail fibres, the baseplate or the capsid of the bacteriophage T4. A protein particularly suitable for the method according to the invention is the GP12 protein of the baseplate, the nucleotide sequence of which is available in the Swissprot (Uniprot) database under accession number [P10930]. Other preferred targeting proteins are GP36 [P03743], GP37 [P03744] and GP38 [P03739], which occur in the distal regions of the tail fibres, or alternatively the proteins of the capsid GP23 [P04535], GP24 [P19896], Hoc [P18056] and Soc [P03715].

Of course, proteins homologous with those mentioned above, present in bacteriophages other than the bacteriophages of type T, are also preferred.

By "homologous sequence", it is meant proteins having an amino acid sequence with at least 50% identity with the latter, preferably at least 70%, more preferably at least 90%.

According to the invention, the bacteriophages are modified at the level of the genes coding for the targeting proteins, by insertion of oligonucleotide sequences produced randomly.

The method according to the invention proves particularly useful for enabling insertion, by homologous recombination, of PCR fragments, which can be introduced in single-stranded form by electroporation.

The period of immobilization of the bacteriophage in the host bacterium is in fact favourable for the integration of such fragments, provided, however, that said fragments comprise, at least partly, sequences homologous with those of the bacteriophage genome.

In this respect, reference will be made to the PCR technique described in the applicant's previous application WO 2008/093010, which makes it possible to generate a large number of copies of DNA fragments comprising, on the one hand, random sequences, and on the other hand, conserved homologous sequences enabling the genes of the bacteriophage to be targeted. These DNA fragments can have a size from 20 to 4000 kb, preferably from 30 to 2000 kb, and more preferably from 40 to 100 kb.

The method according to the invention makes it possible to use a wide variety of PCR products directly and therefore omits the often inevitable step of cloning these fragments. However, such fragments can also be cloned on homologous recombination vectors without affecting the method according to the invention.

According to a preferred aspect of the invention, several genes coding for targeting proteins of the bacteriophage are modified simultaneously by homologous recombination during the immobilization phase of the bacteriophage according to step iii) of the method described above. To achieve such a result, the invention in particular envisages transforming the host bacterium successively or concomitantly, by electroporation of different DNA fragments, preferably targeting different genes.

Preferred vectors for modifying the genes of the bacteriophage T4 according to the invention in the host bacterium E. coli are, for example, the vectors pACYC184 (ATCC 37033), pBAD18-K (ATCC 87397) and RR1 (ATCC 87076). Such vectors have the advantage of possessing markers conferring resistance to different antibiotics. Moreover, they do not share common nucleotide sequences that may cause recombinations between the different vectors, once the latter are integrated in the host bacterium.

According to the invention, modification of the bacteriophages is carried out during a single lytic cycle, the duration of which is prolonged artificially by immobilizing the bacteriophage in the host bacterium.

The progeny of the bacteriophages, obtained at the end of this lytic cycle, generally comprises more than 10%, preferably more than 20%, more preferably more than 50% of genetically modified bacteriophages. This progeny can be reused for a second cycle of reinfection.

Advantageously, in the case of modification of the targeting proteins of the bacteriophages, the modified bacteriophages are collected at the end of the first lytic cycle. In fact, with limitation to a single replication cycle, the bacteriophages display maximum diversity, which would be less if further cycles of reinfection were implemented.

A bank of bacteriophages according to the invention comprises bacteriophages for which one or more targeting proteins are diversified. Such bacteriophages can potentially recognize new bacterial strains. They represent a potential means of combating emerging bacteria or strains that have become resistant to antibiotics.

One aspect of the invention consists of using these genetically modified bacteriophages as antibacterial agents, in particular in the medical field, for treating bacterial infections.

More generally, the invention relates to a bacteriophage genome modified according to the method of the present invention, as well as the genetically modified bacteriophages that may result therefrom.

The invention also relates to modified proteins, which can be extracted from the bacteriophages modified according to the invention, or expressed recombinantly from the DNA obtained from this bacteriophage or from the host bacterium in which it was immobilized. Such a modified protein is preferably a targeting protein of the bacteriophage.

The examples given below aim to illustrate the invention without limiting its scope.

Examples

1/ Construction of a Host Bacterium (No. 1) DK8-Rho*-λ for "Immobilizing" the Bacteriophaqe T4

Step 1: Preparation of the Mutated Rho Gene in an Expression Vector

A copy of the rho gene is amplified by PCR from mutated rho* genes of E. coli coding respectively for the Rho* proteins G51 V, Y800 and Y274D [J. Mol. Biol. (2007) 371 (4):855-872]. Amplification is carried out using the following primers:

```
                                                 (SEQ ID No. 1)
    Rho F: 5' CACCATGAATCTTACCGAATTAAAGAATACG 3'

(SEQ ID No. 2)
    Rho R: 5' TTATGAGCGTTTCATCATTTCGA 3'
```

After purification on preparative agarose gel, the PCR product (Rho*) is cloned into the expression vector pHSG299 under control of a lac promoter inducible by IPTG, using the restriction enzymes EcoRI and SalI. After ligation, the vector pHSG299rho* is purified, resuspended in ddH$_2$O and is used for transforming "electrocompetent" DK8 cells (ATCC 47038). The transformants are selected in LB medium containing 30 µg/ml of kanamycin and are cultured overnight at 30° C. Some colonies are taken for PCR verification of the presence of the insertion segment rho*. The positive colonies are cultured in LB medium+Km for preparing a concentrated culture of DK8-Rho* cells.

Step 2: Construction of E. coli "Mini-λ" Host Bacterium

In order to obtain the effective recombination of the DNA donor in recA$^+$ or recA$^-$ backgrounds, DK8 host bacteria of E. coli containing a prophage λ bearing the recombinant genes exo, bet and gam under the control of a temperature-sensitive λ cI repressor are prepared. The genes exo, bet and gam are activated at 42° C. and repressed at 32° C. When the λ functions are activated for a time reduced to 5 min, the cells become more recombinogenic and absorb the linear DNA without destruction. The Gam protein encoded by λ inhibits attack of the linear DNA by the E. coli nuclease RecBCD, whereas Exo and Beta give rise to recombination activity for this linear DNA. This recombination is much more effective for DNA homologies limited to 30 to 50 bp at the ends of the linear DNAs.

The oligonucleotides 5' GTATGCATGCTGGGTGTGG (MARf) (SEQ ID No. 3) and 5' CGCACTCTCGATTCGTA-GAGCCTCG (MARr) (SEQ ID No. 4) are used as primers for amplification of the prophage λ cI857.

Once the prophage λ has been amplified by PCR, it is cloned, at the SmaI site (blunt end), in the plasmid pFN476 (ATCC86962), which is a reduced copy number plasmid, containing the lac promoter inducible by IPTG. After ligation, the DNA is purified, resuspended in ddH$_2$O and transformed into the DK8-rho* cells previously obtained by electroporation [Sambrook, J. and D. W. Russell (2001) Molecular cloning: a laboratory manual, 3rd ed. Cold Spring Harbor Laboratory Press, Plainview, N.Y.]. After recovery, the cells are spread on plates of LB medium X-gal+Kan+Amp and incubated at 30° C.

Some blank colonies are selected for PCR verification of the presence of the prophage λ. A positive colony is then cultured overnight at 30° C. in LB medium X-Gal+Kan+Amp for preparing a concentrated culture of (DK8-rho*-K) cells.

In this step, the transformed hosts are inducible by λ at 42° C. (high temperature), are lacZ-positive and contain copies of the rho*gene.

2/ Immobilization of the Bacteriophage T4 in the Host Bacterium No. 1

A fresh culture of DK8-rho*-λ cells is cultured overnight in LB medium X-Gal+Kan+Amp at 30° C.

The cultures for infection by T4 are started with a volume less than or equal to 0.05 ml of cells obtained from an overnight culture for 10 ml of LB medium+Kan+Amp in order to guarantee that the cells enter the exponential growth phase before the addition of the bacteriophage.

In order to improve aeration, these cultures are multiplied in 250-ml Erlenmeyer flasks with a side arm, stoppered non-hermetically, in a shaken water bath at 30° C.

250 ml of cells in LB medium X-Gal+Kan+Amp with 1 mM of IPTG (inducer of the expression of rho*) are cultured at a density of 3×10$^8$ cells per ml at 30° C. with agitation by shaking.

The bacteriophage T4 is added at a multiplicity of about 10 particles per cell and growth continues for exactly 20 min.

The cells are spread on plates of LB medium X-gal+Kan+Amp+IPTG and incubated at 30° C.

Figure 1:
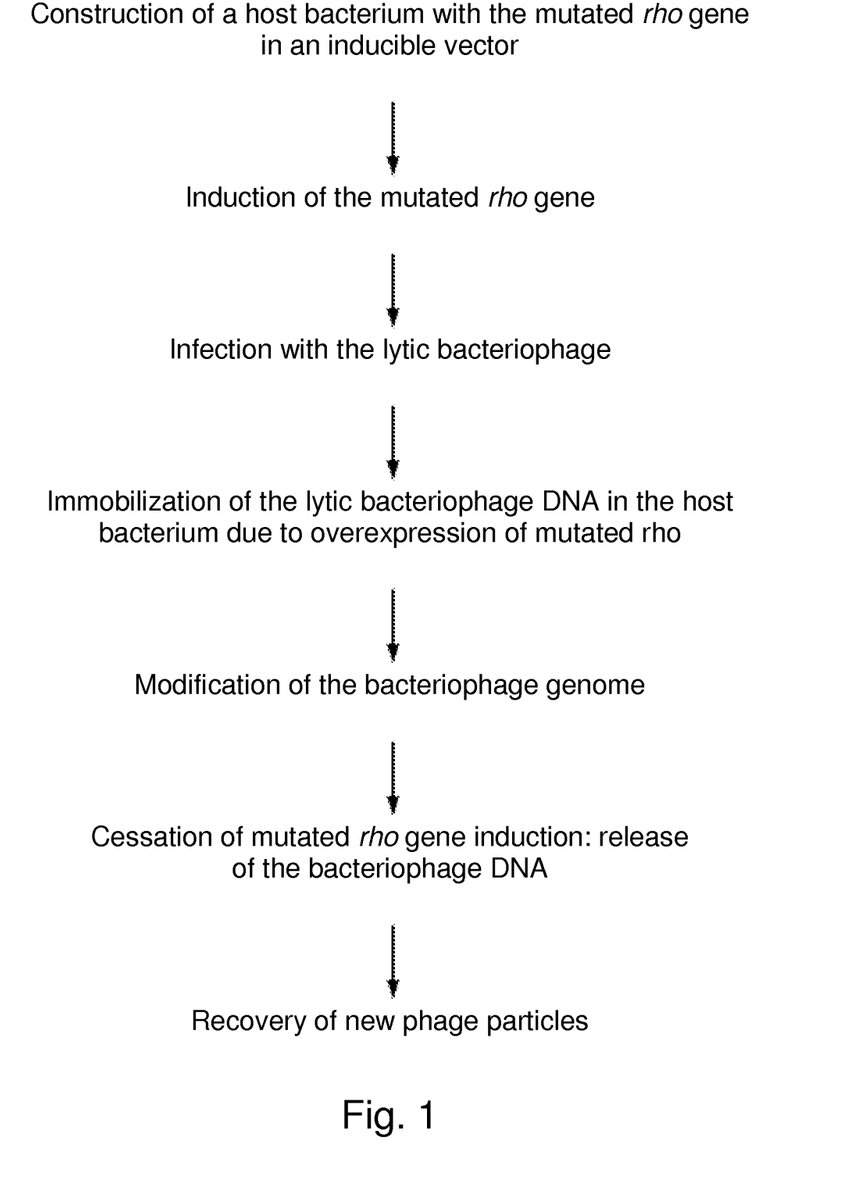
FIG. 1: Synoptic diagram of the steps of the method according to a preferred embodiment of the invention.
Figure 2:
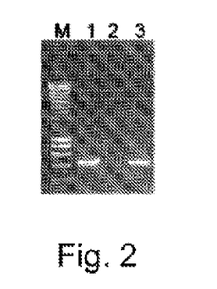
FIG. 2: Verification on agarose gel of the presence of the DNA genome of the bacteriophage T4 in its bacterial host *E. coli* DK8. The DNA is extracted from the bacteria after infection thereof with the bacteriophage T4 and induction of the expression of Rho* in the bacterium. M: SmartLadder molecular size markers (Eurogentec). 1: Control DNA of the bacteriophage T4. 2: Extraction of uninfected *E. coli* cells (negative control). 3: Extraction of the genome of the bacteriophage T4 from the *E. coli* cells, 24 hours after the induction of Rho*. The bacteriophage DNA is detected in wells 1 and 3.
Figure 3:
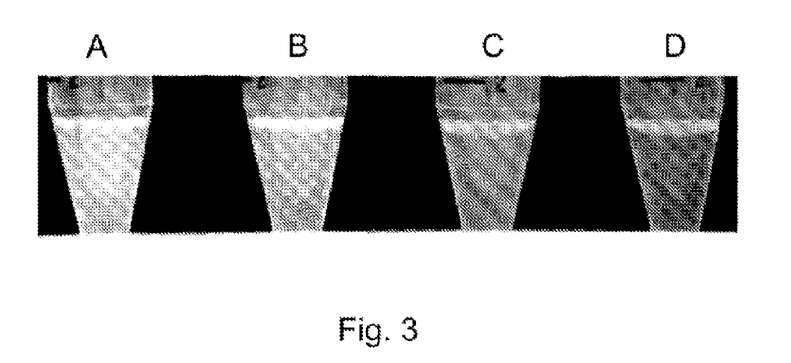
FIG. 3: Suspensions of bacterial cultures of *E. coli* infected with the bacteriophage T4. A: cloudy appearance of the suspension of cells (not lysed). B and C: increasingly clear appearance of the suspension due to cell lysis following removal of immobilization and release of the progeny of the bacteriophage. D: clear appearance of the suspension due to complete lysis of the cells in the absence of the induction of the expression of the Rho* gene. The immobilized phage released remains infectious.
Figure 4:
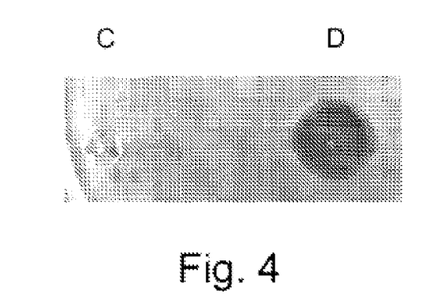
FIG. 4: Deposition on bacterial lawn (in double layer on agar medium). The lysis plaques, which are darker, reveal the presence of bacteriophages at the lytic stage. C: The bacteriophages are in the immobilization phase (absence of lysis plaque). D: The immobilization phase is removed. The bacteriophages then resume their lytic cycle (lysis of the bacteria visible on the bacterial lawn).
Figure 5:
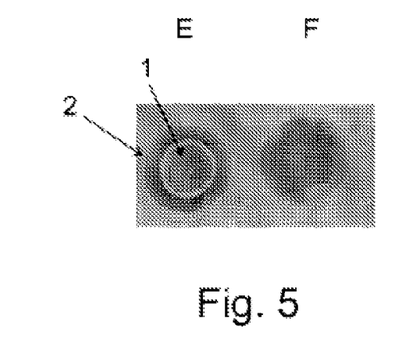
FIG. 5: Deposition on bacterial lawn (in double layer on agar medium). The lysis plates, which are darker, reveal the presence of bacteriophages at the lytic stage. E: (1) bacteria in which the bacteriophages are immobilized (2) bacteriophages released after modification of their genome. F: Release of the bacteriophages after modification.

Some colonies are selected for PCR verification of the presence of the bacteriophage T4 DNA (cf. FIG. 2). A positive colony of the bacteriophage T4 is then cultured overnight at 30° C. in LB medium X-Gal+Kan+Amp+IPTG to prepare a concentrated culture of (DK8-Rho*-λ-DNAT4) cells to be used in subsequent manipulations.

3/Production No. 1 of the Modified Progeny of the Bacteriophage T4

The DK8-Rho*-λ-DNA T4 cells are cultured in liquid medium, then transformed by electroporation according to the usual protocol [Sambrook, J. and D. W. Russell (2001) Molecular cloning: a laboratory manual, 3rd ed. Cold Spring Harbor Laboratory Press, Plainview, N.Y.] using DNA fragments obtained directly from a purified PCR. The PCR fragments comprise modified fragments of the gp37, gp12 and gp38 genes described in WO 2008/093010.

After transformation, the transformed bacteria are cultured on LB medium X-Gal+Kan+Amp+IPTG preheated to 42° C. The cells are incubated for exactly 15 min at 42° C. with constant aeration. The cultures are then transferred to a water bath at 30° C., allowing growth to continue for exactly 25 min.

The aim of this step is to induce homologous recombination between the PCR fragments introduced and the DNA of the bacteriophage T4 present in the bacterium.

Once recombination has been performed, the DK8-Rho*-λ-DNA cells are resuspended and washed in LB medium+Kan+Amp, then incubated for exactly 2 hours at 30° C. During this incubation, the bacteria are lysed and release the progeny of the bacteriophage T4. This progeny is composed, partly, of modified bacteriophages.

The lysed bacteria are collected by centrifugation at 5000 rpm for 5 minutes whereas the lysis supernatant is recovered. Some drops of chloroform are added to the supernatant, the latter is centrifuged again for 10 min at 6000 rpm. The chloroform is removed. Then the supernatant, which contains the modified bacteriophages, is adjusted to a buffer concentration SM 1× (MgSO$_4$10 mM, NaCl 100 mM, 0.01% of gelatin and Tris-HCl 50 mM [pH 7.5]) using concentrated buffer 5×, to be stored at 4° C.

4/Construction of a Host Bacterium (No. 2) for "Immobilizing" the Bacteriophage T4 on a Plasmid The aim of this construction is to clone the genome of the bacteriophage T4 into a vector, once said genome is immobilized in the bacterium.

Insertion into the vector is carried out by homologous recombination at the level of the sequence of the mobA gene present in the bacteriophage genome.

Step 1: Preparation of a Vector Comprising a Copy of the mobA Gene of the Bacteriophage T4

The mobA gene is amplified by PCR starting from genomic DNA of the bacteriophage T4 using the following primers:

```
                                              (SEQ ID No. 5)
    mobA F:  5' GTAGAAAATAGTGCTAAAAAGTGT 3'

(SEQ ID No. 6)
    mobA R:  5' TTAATAGTGCGGGGTAAAACCC 3'
```

After purification on preparative agarose gel, the PCR product (mobA) is cloned between two loxP sites of the vector pDNR-1r at the SmaI cleavage site. *E. coli* DK8 cells (ATCC 47038) are then transformed using the vector pDNR-1rmobA which bears a chloramphenicol (Cm) resistance gene. The transformants are selected in LB medium at 37° C. containing 30 µg/ml of chloramphenicol. After verification, the transformants (DK8-mobA) are used for preparing a stock of pDNR-1 rmobA vector.

Step 2: Introduction of the pDNR-1 rmobA Vector into DK8-Rho*-λ Cells

The DK8-Rho*-λ cells are made "electrocompetent" according to the protocol mentioned in point 3/ above, then transformed using the pDNR-1 rmobA vector prepared above.

The transformed cells are spread on plates of LB medium X-Gal+Kan+Amp+Cm, then incubated at 30° C.

Some colonies are selected for PCR verification of the presence of the pDNR-1 rmobA vector. A positive colony is then cultured overnight at 30° C. in LB medium X-Gal+Kan+Amp+Cm to prepare a concentrated culture of cells (DK8-Rho*-λ-mobA) which can be used in subsequent manipulations.

5/ Immobilization of the Bacteriophage T4 in the Host Bacterium No. 2

A fresh overnight culture of DK8-Rho*-λ-mobA cells is prepared in LB medium X-Gal+Kan+Amp+Cm at 30° C.

The cultures to be infected with the bacteriophage T4, are started with a volume less than or equal to 0.05 ml of cells of an overnight culture for 10 ml of LB medium X-Gal+Kan+Amp+Cm in order to guarantee that the cells enter the exponential growth phase before the addition of said bacteriophage.

In order to improve aeration, these cultures are multiplied in 250-ml Erlenmeyer flasks with a side arm, stoppered non-hermetically, in a shaken water bath at 30° C.

250 ml of cells in LB medium X-Gal+Kan+Amp+Cm are cultured with IPTG, the inducer of Rho* expression at a density of 3×10$^8$ cells per ml at 30° C. with agitation by shaking.

10-ml aliquots of cells in exponential growth are then transferred to 40 ml of LB medium X-Gal+Kan+Amp+Cm preheated to 42° C. and incubated for exactly 15 min at 42° C. with constant aeration. The bacteriophage T4 is added at a multiplicity of about 10 particles per cell. The cultures are transferred to a water bath at 30° C., allowing growth to continue for exactly 25 min.

The cells are spread on plates of LB medium X-Gal+Kan+Amp+Cm+IPTG and incubated at 30° C.

Some colonies are selected for PCR verification of the presence of the bacteriophage T4 DNA. A positive colony of the bacteriophage T4 is then cultured overnight at 30° C. in LB medium X-Gal+Kan+Amp+Cm+IPTG to prepare a concentrated culture of cells (DK8-Rho*-λ-mobA-DNA T4) to be used in subsequent manipulations.

6/ Production No. 2 of Progeny of Bacteriophage T4 with Modifications

In order to release the bacteriophage genome from the pDNR-1rmobA plasmid, another plasmid pHSG-cre (ATCC No. 87075) expressing the Cre protein is introduced into DK8-Rho*-λ-mobA-DNA T4 cells. This plasmid is introduced following the same electroporation protocol as before. The induction of Rho* in the host bacterium is stopped. To do this, the cells are centrifuged, the medium is withdrawn and the bacterial pellet is washed with LB medium without inducer. Expression of the protein Cre then leads to recombination at the loxP sites of the vector pDNR-1 rmobA-T4, and thus release of the complete genomic DNA of the bacteriophage T4.

The cells are then incubated for exactly 2 hours at 30° C. in LB X-Gal+Kan+Amp+Cm. During this incubation, the bacteriophages resume their lytic cycle: the bacteria are lysed and release the progeny of the bacteriophage T4.

The bacteriophage are recovered by centrifugation in the same way as in point 3/.

---

The invention claimed is:

1. Method for modifying the genome of a lytic bacteriophage in a host bacterium, characterized in that:
   (i) a host bacterium is infected with a bacteriophage;
   (ii) the lytic cycle of the bacteriophage is inhibited in the host bacterium;
   (iii) the bacteriophage genome is modified during step ii) during which the bacteriophage is immobilized in the host bacterium;
   (iv) the inhibition of step ii) of the lytic cycle is removed, so as to release the progeny of the bacteriophage of step (i), the genome of which was modified.

2. Method according to claim 1, characterized in that the lytic bacteriophage is a bacteriophage of the Myoviridae family.

3. Method according to claim 1, characterized in that the lytic cycle of the bacteriophage is inhibited in the host bacterium in step ii) by overexpression, in the cytoplasm of the bacterium, of the Rho protein of the bacterium, in a non-functional form (Rho*).

4. Method according to claim 3, characterized in that Rho* proteins are overexpressed by means of a mutated copy of the rho gene under the control of an inducible promoter.

5. Method according to claim 4, characterized in that the host bacterium in step iii) undergoes a step of bacterium transformation, in particular by the action of an electric field (electroporation), so that the latter integrates exogenous nucleic acid sequences.

6. Method according to claim 5, characterized in that said nucleic acid sequences comprise oligonucleotide sequences produced by PCR or homologous recombination vectors.

7. Method according to claim 5, characterized in that modification of the bacteriophage genome in step iii) in the host bacterium is carried out by homologous recombination by means of a vector, after transformation of the host cell by this vector.

8. Method according to claim 1, characterized in that the bacteriophage genome is integrated in a replication vector during step iii).

9. Method according to claim 1, characterized in that the host bacterium is allowed to divide whereas the bacteriophage is immobilized therein between steps ii) and iv).

10. Method according to claim 1, characterized in that it comprises the following steps:
   i) culturing a host bacterium possessing a rho gene, as well as a mutated copy of said gene (rho*), the expression of which is optional;
   ii) inducing the expression of the mutated rho* gene in the host bacterium;
   iii) infecting said host bacterium in which the mutated rho* gene is expressed by means of a lytic bacteriophage specific to it, this having the effect of immobilizing the bacteriophage in its host bacterium;
   iv) modifying the bacteriophage genome within the host bacterium during step iii);
   v) ceasing induction of the expression of rho*, allowing the wild-type rho gene to be expressed in the bacterium, which has the effect of removing the immobilization of the bacteriophage and releasing the progeny of the bacteriophage, the genome of which was modified.

11. Method according to claim 1, characterized in that the genome of said bacteriophage is modified in step iii) at the level of a gene expressing a targeting protein.

12. Method according to claim 11, characterized in that said targeting protein is selected from GP12, GP36, GP37 and GP38 or a protein that is homologous with the latter.

13. Method according to claim 1, characterized in that the genome of said bacteriophage is modified in step iii) at the level of a gene expressing a capsid protein of the bacteriophage.

14. Method according to claim 13, characterized in that said capsid protein is selected from GP23, GP24, Hoc and Soc or a protein that is homologous with the latter.

* * * * *